(12) United States Patent
Coombs et al.

(10) Patent No.: US 9,841,836 B2
(45) Date of Patent: Dec. 12, 2017

(54) CONTROL OF NON-DESTRUCTIVE TESTING DEVICES

(71) Applicant: General Electric Company, Schenectady, NY (US)

(72) Inventors: Kevin Andrew Coombs, Syracuse, NY (US); Thomas C. Ward, Auburn, NY (US); Melissa Rose Stancato, Syracuse, NY (US); Nicolas Anthony Stancato, Syracuse, NY (US); Joseph John Waclawski, Baldwinsville, NY (US)

(73) Assignee: General Electric Company, Schenectady, NY (US)

( * ) Notice: Subject to any disclaimer, the term of this patent is extended or adjusted under 35 U.S.C. 154(b) by 4 days.

(21) Appl. No.: 14/811,642

(22) Filed: Jul. 28, 2015

(65) Prior Publication Data

US 2017/0031492 A1    Feb. 2, 2017

(51) Int. Cl.
| | |
|---|---|
| *G06F 3/041* | (2006.01) |
| *G06F 3/00* | (2006.01) |
| *G06F 3/01* | (2006.01) |
| *G01N 21/954* | (2006.01) |
| *H04N 5/232* | (2006.01) |

(52) U.S. Cl.
CPC ......... *G06F 3/0416* (2013.01); *G01N 21/954* (2013.01); *G06F 3/005* (2013.01); *G06F 3/017* (2013.01); *G06F 2203/04104* (2013.01); *H04N 5/23216* (2013.01); *H04N 5/23245* (2013.01)

(58) Field of Classification Search
CPC ........ G01N 21/954; G06F 2203/04104; G06F 3/005; G06F 3/017; G06F 3/0416; H04N 5/23216; H04N 5/23245

USPC ......................................... 345/156, 170-176
See application file for complete search history.

(56) References Cited

U.S. PATENT DOCUMENTS

| | | | | |
|---|---|---|---|---|
| 9,152,304 B2* | 10/2015 | Schiefer | ................ | G06F 3/0484 |
| 2007/0100214 A1* | 5/2007 | Steinert | .................... | A61H 1/00 600/300 |
| 2013/0033435 A1* | 2/2013 | Raveendran | .......... | G06F 3/0481 345/173 |
| 2014/0184524 A1* | 7/2014 | Schiefer | ................ | G06F 3/0484 345/173 |
| 2014/0188423 A1* | 7/2014 | Messinger | ............. | G01B 15/00 702/108 |
| 2014/0188435 A1* | 7/2014 | Coombs | ................ | G05B 23/00 702/188 |
| 2014/0268541 A1* | 9/2014 | Coombs | .................... | H05K 7/00 361/679.41 |
| 2016/0011740 A1* | 1/2016 | Schiefer | ................ | G06F 3/0484 345/173 |

(Continued)

*Primary Examiner* — Tony Davis
(74) *Attorney, Agent, or Firm* — Fletcher Yoder, P.C.

(57) ABSTRACT

A non-transitory, computer-readable medium includes computer-executable code having instructions. The instructions are configured to receive data relating to an environment, construct an image of the environment based on the received data, and display the image on a touch-screen device. The instructions are also configured to receive a control gesture via the touch-screen device and interpret the control gesture. Further, the instructions are configured to control an articulating system coupled to the device to control an orientation of a sensor configured to collect the data, control a mode of operation of the sensor, or any combination thereof based on the interpretation of the control gesture.

20 Claims, 7 Drawing Sheets

(56) References Cited

U.S. PATENT DOCUMENTS

2016/0091968 A1\* 3/2016 Angelo .................. G06F 3/011
 345/156

\* cited by examiner

CONTROL OF NON-DESTRUCTIVE TESTING DEVICES

BACKGROUND

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support. During equipment operations, the equipment may degrade, encounter undesired conditions such as corrosion, wear and tear, and so on, potentially affecting overall equipment effectiveness. Certain inspection techniques, such as non-destructive inspection techniques or non-destructive testing (NDT) techniques, may be used to detect undesired equipment conditions. It would be beneficial to improve control of NDT devices.

BRIEF DESCRIPTION

Certain embodiments commensurate in scope with the originally claimed disclosure are summarized below. These embodiments are not intended to limit the scope of the claimed disclosure, but rather these embodiments are intended only to provide a brief summary of possible forms of the disclosure. Indeed, the full disclosure may encompass a variety of forms that may be similar to or different from the embodiments set forth below.

The techniques described herein provide for a variety of gestures, such as touch-based gestures, that may be used to control certain NDT devices. For example, a user may place a finger on a portion of a touchscreen included in a video borescope and move the finger a certain distance on the touchscreen. The movement may be interpreted by a processor of the video borescope as a control action to move the borescope probe a desired distance. The desired distance may be derived based on, for example, the position of the finger relative to a center of the touchscreen. Other such gestures are described in more detail below.

In a first embodiment, a non-destructive testing (NDT) system includes a sensor configured to collect data about a surrounding environment. The NDT system also includes an articulating system configured to move the sensor and a touchscreen configured to display a user interface and an image of the surrounding environment based on the collected data, wherein the touchscreen is configured to receive a plurality of control gestures. Further, the NDT system includes a processor configured to interpret each of the plurality of control gestures and control the articulating system to move the sensor based on the interpretation of the plurality of control gestures.

In a second embodiment, a method includes collecting, via a non-destructive testing (NDT) system, data about a surrounding environment using a sensor; constructing, via the NDT system, an image of the surrounding environment based on the collected data; and displaying the image on a touchscreen system. The method also includes receiving, via the touchscreen system, a control gesture as a user input; interpreting the control gesture; and actuating, via the NDT system, an articulating system coupled to the sensor. The articulating system may be controlled in order to control an orientation of the sensor; control a mode of operation of the sensor; or any combination thereof based on the interpretation of the control gesture.

In a third embodiment, a non-transitory, computer-readable medium includes computer-executable code having instructions. The instructions are configured to receive data relating to an environment, construct an image of the environment based on the received data, and display the image on a touch-screen device. The instructions are also configured to receive a control gesture via the touch-screen device and interpret the control gesture. Further, the instructions are configured to control an articulating system coupled to the device to control an orientation of a sensor configured to collect the data, control a mode of operation of the sensor, or any combination thereof based on the interpretation of the control gesture.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
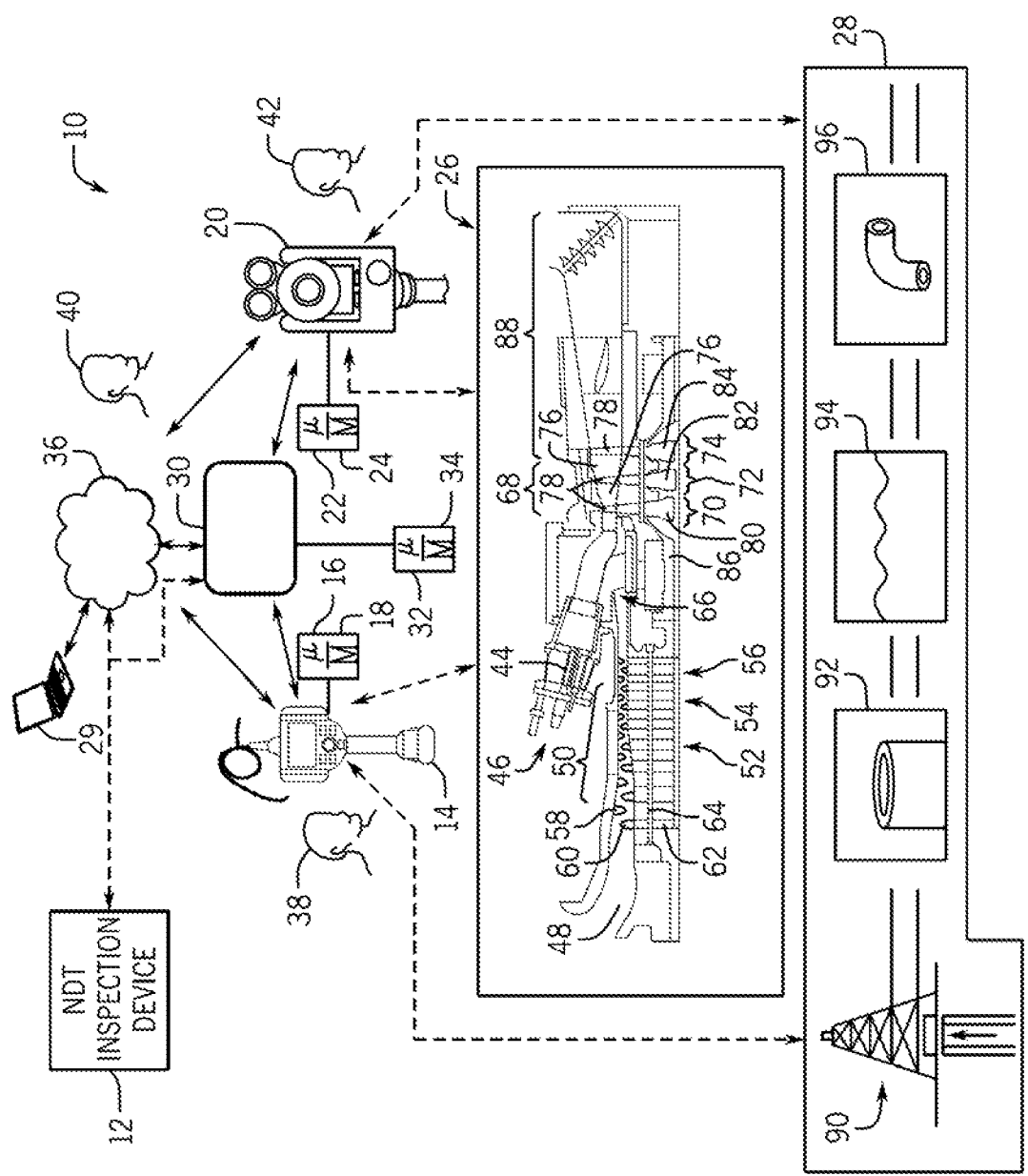
FIG. 1 is a block diagram illustrating an embodiment of an exemplary distributed non-destructive testing (NDT) system, including devices configured to be controlled using relative control gestures, in accordance with an embodiment of the present approach.

Embodiments of the subject matter disclosed herein generally relate to non-destructive testing (NDT) systems and devices, which may be used to inspect a variety of equipment and facilities (e.g., industrial equipment and facilities, power generation equipment and facilities, and aircraft equipment and facilities). The NDT systems and devices may be used to inspect equipment and facilities by collecting images and data of the equipment and facilities as well as inside the equipment and facilities. Accordingly, certain embodiments of the disclosed subject matter may relate to control schemes for controlling NDT systems and devices. In particular, some embodiments of the disclosed subject matter may utilize relative control gestures, which may allow an operator to control, for example, an NDT device based on the type of gesture used and proximity of the gesture relative to a point on the device or image displayed on the device. In certain embodiments, the relative control gestures may be used primarily on a touchscreen associated with the NDT system or device, and may be used to control the NDT system or device in various modes of operation. Other embodiments are within the scope of the disclosed subject matter.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements.

Non-destructive testing (NDT) devices and systems may be used to inspect various equipment and facilities, such as power generation equipment and facilities, oil and gas equipment and facilities, aircraft equipment and facilities, and manufacturing equipment and facilities. NDT devices and systems typically include measurement devices (e.g., sensors) and cameras that may be inserted into various locations in or around the equipment and facilities. The measurement devices and cameras are remotely coupled to other devices that an operator may use to view the data gathered by the measurement device and camera as well as control the measurement device and camera.

As such, an NDT device or system may include a physical joystick, a virtual joystick, a control pad, or a combination thereof that allows the operator to control or otherwise position the attached sensor (e.g., measurement device and/or camera sensor). To increase the number of control actions assigned to the NDT control system, as well as to increase the customization of control actions, the NDT device or system may use a set of relative control gestures (e.g., touch gestures). In particular, the relative control gestures can be mapped to different control actions for controlling the orientation and movement of an NDT device or system as well as multiple modes of operation for the NDT device or system. In certain embodiments, the relative control gestures may be used to switch between the different modes of operation.

Operators may also reconfigure the relative control gestures in various ways. For instance, operators may reassign the control actions assigned to certain relative control gestures. Operators may also reconfigure the relative control gestures to use multiple fingers and hands, and to create an approximation of a "hot corners" mechanism. The relative control gestures may also account for sensitivity control, particular when the control gestures are used for touchscreen operation of an NDT device or system.

Some example relative control gestures include a single tap on an NDT screen to jog (bump) a probe to articulate in the direction of the tap relative to the center of the screen. A press and hold could command the NDT system to move continuously in the direction of the press and hold. While still holding, a user could slide their finger to a different location, giving the articulation section of the NDT device a new command. Tapping with a second finger during this time could toggle "steer-and-stay," as described in more detail below. A two finger tap could be additionally available at any time to toggle steer-and-stay on and off. A single-finger, double-tap on the screen could toggle a freeze frame function. Indeed, a variety of gestures may be provided, as described herein.

With the foregoing in mind, FIG. 1 depicts a block diagram of an embodiment of distributed NDT system 10. In the depicted embodiment, the distributed NDT system 10 may include one or more NDT inspection devices 12. The NDT inspection devices 12 may be divided into at least two categories. In one category, depicted in FIG. 1, the NDT inspection devices 12 may include devices suitable for visually inspecting a variety of equipment and environments. In another category, described in more detail with respect to FIG. 2 below, the NDT devices 12 may include devices providing for alternatives to visual inspection modalities, such as x-ray inspection modalities, eddy current inspection modalities, and/or ultrasonic inspection modalities.

In the depicted first example category of FIG. 1, the NDT inspection devices 12 may include a borescope 14 having one or more processors 16 and a memory 18, and a transportable pan-tilt-zoom (PTZ) camera 20 having one or more processors 22 and a memory 24. In this first category of visual inspection devices, the borescope 14 and PTZ camera 20 may be used to inspect, for example, a turbo machinery 26, and a facility or site 28. As illustrated, the borescope 14 and the PTZ camera 20 may be communicatively coupled to a mobile device 30 also having one or more processors 32 and a memory 34. The mobile device 30 may include, for example, a tablet, a cell phone (e.g., smart phone), a notebook, a laptop, or any other mobile computing device. Accordingly, in one embodiment, the mobile device 30 may be the tablet mentioned above, available from General Electric Co., of Schenectady, N.Y., and providing for touchscreen input. The mobile device 30 may be communicatively coupled to the NDT inspection devices 12, such as the borescope 14 and/or the PTZ camera 20, through a variety of wireless or wired conduits. For example, the wireless conduits may include WiFi (e.g., Institute of Electrical and Electronics Engineers [IEEE] 802.11X), cellular conduits (e.g., high speed packet access [HSPA], HSPA+, long term evolution [LTE], WiMax), near field communications (NFC), Bluetooth, personal area networks (PANs), and the like. The wireless conduits may use a variety of communication protocols, such as TCP/IP, UDP, SCTP, socket layers, and so on. In certain embodiments, the wireless or wired conduits may include secure layers, such as secure socket layers (SSL), virtual private network (VPN) layers, encrypted layers, challenge key authentication layers, token authentication layers, and so on. Wired conduits may include proprietary cabling, RJ45 cabling, co-axial cables, fiber optic cables, and so on.

Additionally or alternatively, the mobile device 30 may be communicatively coupled to the NDT inspection devices 12, such as the borescope 14 and/or the PTZ camera 20, through the "cloud" 36. Indeed, the mobile device 30 may use the cloud 36 computing and communications techniques (e.g., cloud-computing network), including but not limited to HTTP, HTTPS, TCP/IP, service oriented architecture (SOA) protocols (e.g., simple object access protocol [SOAP], web services description languages (WSDLs)) to interface with the NDT inspection devices 12 from any geographic location, including geographic locations remote from the physical location about to undergo inspection. Further, in some embodiments, the mobile device 30 may provide "hot spot" functionality in which mobile device 30 may provide wireless access point (WAP) functionality suitable for connecting the NDT inspection devices 12 to other systems in the cloud 36.

The borescope 14 and the PTZ camera may be controlled by a variety of operators located at the inspection site and/or a remote location. For example, a borescope operator 38 may physically manipulate the borescope 14 at one location, while a mobile device operator 40 may use the mobile device 30 to interface with and physically manipulate the borescope 14 at a second location through remote control techniques. The second location may be proximate to the first location or geographically distant from the first location. Likewise, a camera operator 42 may physically operate the PTZ camera 20 at a third location, and the mobile device operator 40 may remote control PTZ camera 20 at a fourth location by using the mobile device 30. The fourth location may be proximate to the third location or geographically distant from the third location. Any and all control actions performed by the operators 38 and 42 may be additionally performed by the operator 40 through the mobile device 30. Additionally, the operator 40 may communicate with the operators 38 and/or 42 by using the devices 14, 20, and 30 through techniques such as voice over IP (VOIP), virtual whiteboarding, text messages, and the like.

In the present embodiments, the borescope operator 38 and/or the camera operator 42 may control the borescope 14 and/or the PTZ camera 20 using relative control gestures (e.g., touch gestures), which are described in more detail below. The relative control gestures may be used on their own or may be combined with inputs derived from other control devices (e.g., physical manipulation device such as a physical joystick, a set of buttons, a physical control pad, and so on). Additionally, the relative control gestures may be combined with control inputs from other external systems, such as a second NDT system, a laptop, cell phone, tablet, and so on. Further, in embodiments in which the mobile device 30 is primarily used to control the borescope 14 and/or the PTZ camera 20, an operator may also use relative control gestures via the mobile device 30. Indeed, the mobile device 30 may be operated alongside or in tandem with the devices 14 and 20 by the operators 38, 40 and 42.

Whether controlled by the operator 38, 40, and/or 42, the borescope 14 and/or PTZ camera 20 may be used to visually inspect a wide variety of equipment and facilities. For example, the borescope 14 may be inserted into a plurality of borescope ports and other locations of the turbomachinery 26, to provide for illumination and visual observations of a number of components of the turbomachinery 26. In the depicted embodiment, the turbomachinery 26 is illustrated as a gas turbine suitable for converting carbonaceous fuel into mechanical power. However, other equipment types may be inspected, including compressors, pumps, turbo expanders, wind turbines, hydroturbines, industrial equipment, and/or residential equipment. The turbomachinery 26 (e.g., gas turbine) may include a variety of components that may be inspected by the NDT inspection devices 12 described herein.

Keeping the foregoing in mind, it may be beneficial to discuss certain turbomachinery 26 components that may be inspected by using the embodiments disclosed herein. For example, certain components of the turbomachinery 26 depicted in FIG. 1, may be inspected for corrosion, erosion, cracking, leaks, weld inspection, and so on. Mechanical systems, such as the turbomachinery 26, experience mechanical and thermal stresses during operating conditions, which may require periodic inspection of certain components. During operations of the turbomachinery 26, a fuel such as natural gas or syngas, may be routed to the turbomachinery 26 through one or more fuel nozzles 44 into a combustor 46. Air may enter the turbomachinery 26 through an air intake section 48 and may be compressed by a compressor 50. The compressor 50 may include a series of stages 52, 54, and 56 that compress the air. Each stage may include one or more sets of stationary vanes 58 and blades 60 that rotate to progressively increase the pressure to provide compressed air. The blades 60 may be attached to rotating wheels 62 connected to a shaft 64. The compressed discharge air from the compressor 50 may exit the compressor 50 through a diffuser section 66 and may be directed into the combustor 46 to mix with the fuel. For example, the fuel nozzles 44 may inject a fuel-air mixture into the combustor 46 in a suitable ratio for optimal combustion, emissions, fuel consumption, and power output. In certain embodiments, the turbomachinery 26 may include multiple combustors 46 disposed in an annular arrangement. Each combustor 46 may direct hot combustion gases into a turbine 68.

As depicted, the turbine 68 includes three separate stages 70, 72, and 74 surrounded by a casing 76. Each stage 70, 72, and 74 includes a set of blades or buckets 78 coupled to a respective rotor wheel 80, 82, and 84, which are attached to a shaft 86. As the hot combustion gases cause rotation of turbine blades 60, the shaft 86 rotates to drive the compressor 50 and any other suitable load, such as an electrical generator. Eventually, the turbomachinery 26 diffuses and exhausts the combustion gases through an exhaust section 88. The disclosed embodiments, such as the NDT inspection devices 12, may be used to inspect and maintain turbine components such as the nozzles 44; intake 48; compressor 50; vanes 58; blades 60; wheels 62; shaft 64; diffuser 66; stages 70, 72, and 74; blades 78; shaft 86; casing 76; and exhaust 88.

Additionally, or alternatively, the PTZ camera 20 may be disposed at various locations around or inside of the turbomachinery 26, and used to procure visual observations of these locations. The PTZ camera 20 may additionally include one or more lights suitable for illuminating desired locations, and may further include zoom, pan and tilt techniques described in more detail below with respect to FIG. 4, useful for deriving observations around in a variety of difficult to reach areas. The borescope 14 and/or the camera 20 may be additionally used to inspect the facilities 28, such as an oil and gas facility 28. Various equipment such as oil and gas equipment 90 may be inspected visually by using the borescope 14 and/or the PTZ camera 20. Advantageously, locations such as the interior of pipes or conduits 92, underwater (or underfluid) locations 94, and difficult to observe locations such as locations having curves or bends 96, may be visually inspected by using the mobile device 30 and the borescope 14 and/or PTZ camera 20. Accordingly, the mobile device operator 40 may more safely and efficiently inspect the equipment 26, 90 and locations 92, 94, and 96, and share observations in real-time or near real-time with locations geographically distant from the inspection areas. It is to be understood that other NDT inspection devices 12 may use the embodiments described herein, such as fiberscopes (e.g., articulating fiberscope, non-articulating fiberscope), and remotely operated vehicles (ROVs), including robotic pipe inspectors and robotic crawlers.

Figure 2:
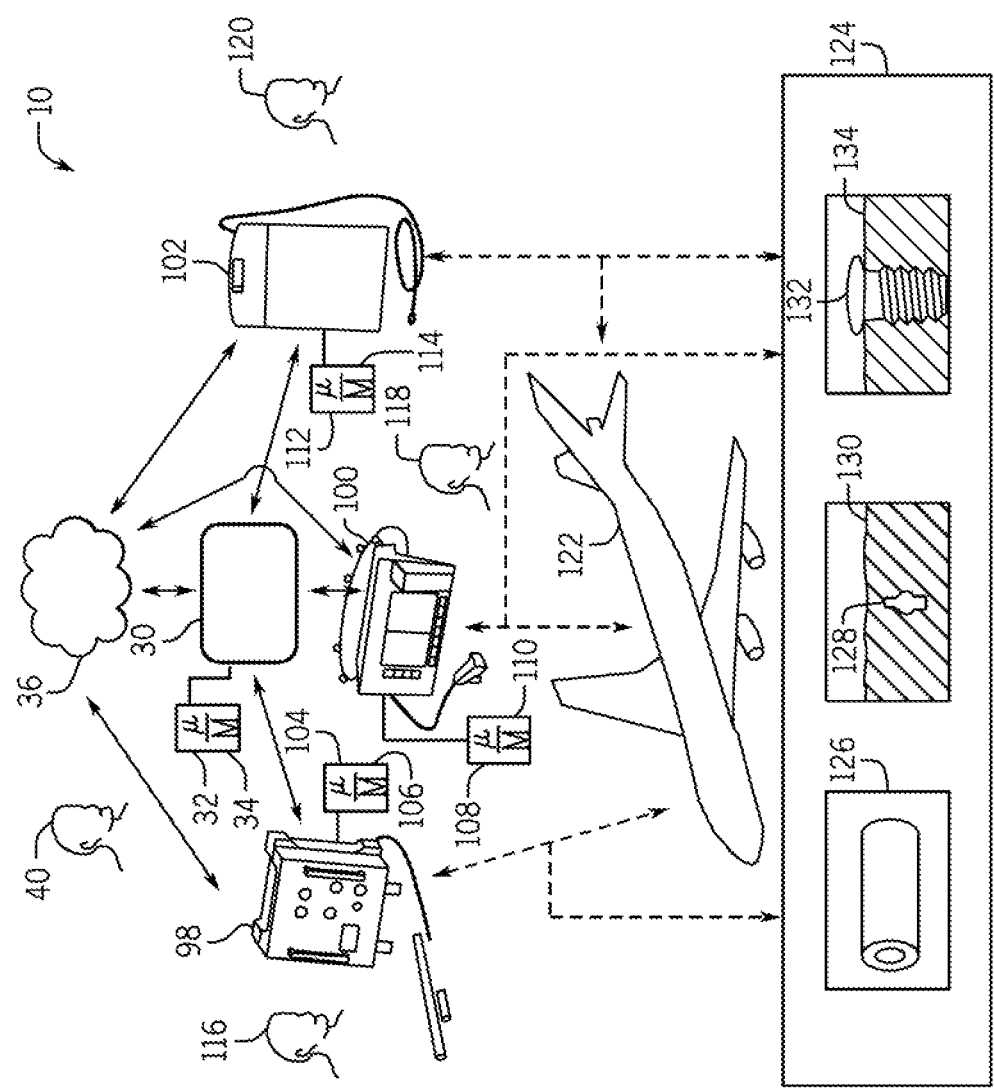
FIG. 2 is a block diagram illustrating further details of an embodiment of the exemplary distributed NDT system of FIG. 1, including devices configured to be controlled using relative control gestures, in accordance with an embodiment of the present approach.

Turning now to FIG. 2, the figure is a block diagram of an embodiment of the distributed NDT system 10 depicting the second category of NDT inspection devices 12 that may be able to provide for alternative inspection data to visual inspection data. For example, the second category of NDT inspection devices 12 may include an eddy current inspection device 98, an ultrasonic inspection device, such as an ultrasonic flaw detector 100, and an x-ray inspection device, such a digital radiography device 102. The eddy current inspection device 98 may include one or more processors 104 and a memory 106. Likewise, the ultrasonic flaw detector 100 may include one or more processors 108 and a memory 110. Similarly, the digital radiography device 102 may include one or more processors 112 and a memory 114. In operations, the eddy current inspection device 98 may be operated by an eddy current operator 116, the ultrasonic flaw detector 100 may be operated by an ultrasonic device operator 118, and the digital radiography device 102 may be operated by a radiography operator 120.

As depicted, the eddy current inspection device 98, the ultrasonic flaw detector 100, and the digital radiography inspection device 102, may be communicatively coupled to the mobile device 30 by using wired or wireless conduits, including the conduits mentioned above with respect to FIG. 1. Additionally, or alternatively, the devices 98, 100, and 102 may be coupled to the mobile device 30 by using the cloud 36. For example, the eddy current inspection device 98 may be connected to a cellular "hotspot," and use the hotspot to connect to one or more experts in eddy current inspection and analysis. Accordingly, the mobile device operator 40 may remotely control various aspects of operations of the devices 98, 100, and 102 by using the mobile device 30, and may collaborate with the operators 116, 118, and 120 through voice (e.g., voice over IP [VOIP]), data sharing (e.g., whiteboarding), providing data analytics, expert support and the like.

Accordingly, it may be possible to enhance the visual observation of various equipment, such as an aircraft system 122 and facilities 124, with x-ray observation modalities, ultrasonic observation modalities, and/or eddy current observation modalities. For example, the interior and the walls of pipes 126 may be inspected for corrosion and/or erosion. Likewise, obstructions or undesired growth inside of the pipes 126 may be detected by using the devices 98, 100, and/or 102. Similarly, fissures or cracks 128 disposed inside of certain ferrous or non-ferrous material 130 may be observed. Additionally, the disposition and viability of parts 132 inserted inside of a component 134 may be verified. Indeed, by using the techniques described herein, improved inspection of equipment and components 122, 126, 130 and 134 may be provided. For example, the mobile device 30 may be used to interface with and provide remote control of the devices 14, 20, 98, 100, and 102.

The devices 98, 100, and 102 may also be operated using the mobile device 30 in a similar manner to the borescope 14 and/or the PTZ camera 20. In particular, all of the devices 14, 20, 98, 100, and 102 may be controlled using relative control gestures, which are described in more detail below. Likewise to the devices 14 and 20, the mobile device 30 may be operated alongside or in tandem with the devices 98, 100, and 102.

Figure 3:
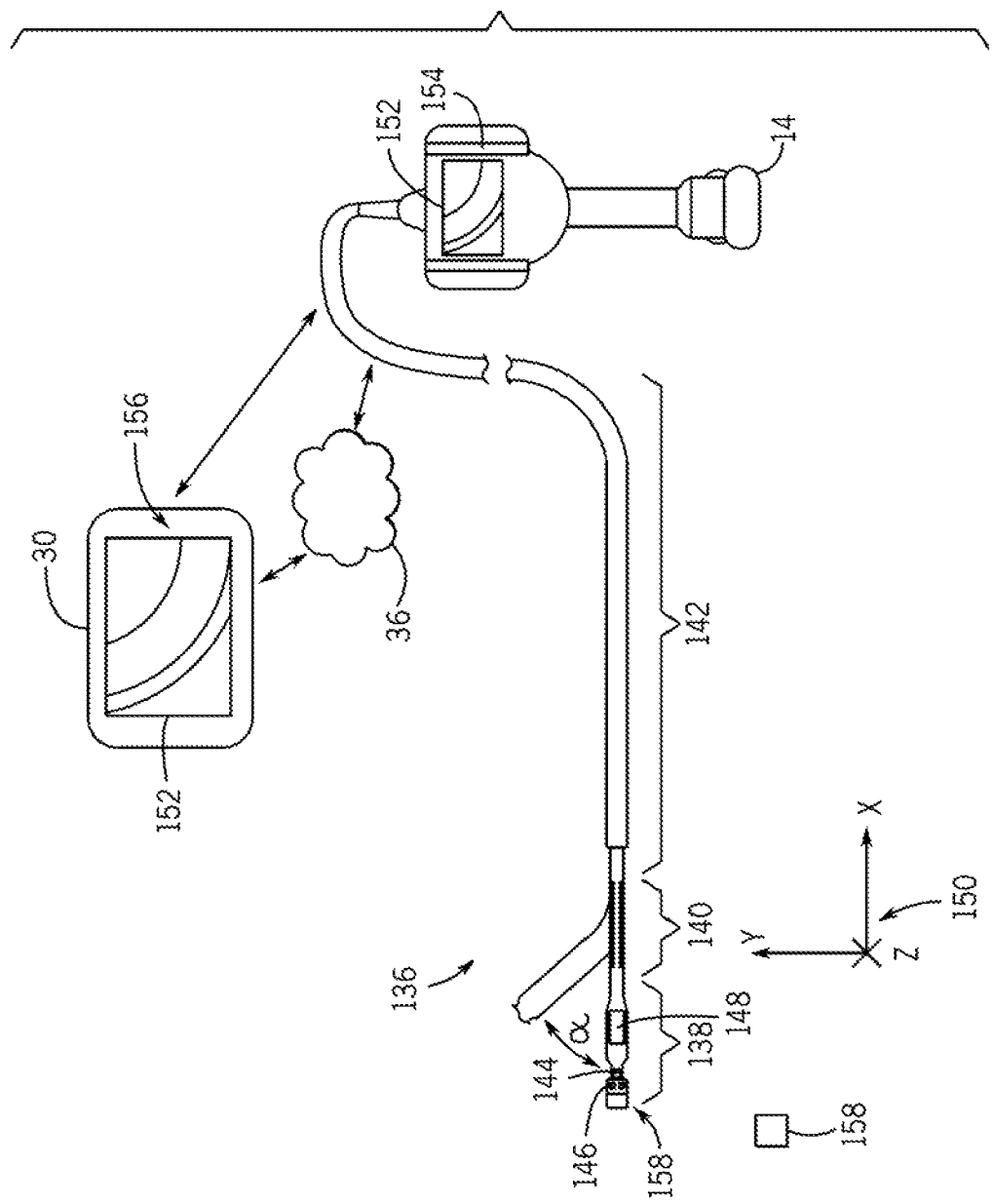
FIG. 3 is a front view illustrating an exemplary embodiment of a borescope communicatively coupled to the mobile device of FIG. 1 and a "cloud," in accordance with an embodiment of the present approach.

FIG. 3 is a front view of the borescope 14 coupled to the mobile device 30 and the cloud 36. Accordingly, the borescope 14 may provide data to any number of devices connected to the cloud 36 or inside the cloud 36. As mentioned above, the mobile device 30 may be used to receive data from the borescope 14, to remotely control the borescope 14, or a combination thereof. For example, a variety of data may be transmitted from the borescope 14 to the mobile device 30, including but not limited to images, video, and sensor measurements, such as temperature, pressure, flow, clearance (e.g., measurement between a stationary component and a rotary component), and distance measurements. Likewise, the mobile device 30 may communicate control instructions (e.g., relative control gestures), reprogramming instructions, configuration instructions, and the like to the borescope 14.

As depicted, the borescope 14 includes an insertion tube 136 suitable for insertion into a variety of locations, such as inside of the turbomachinery 26, equipment 90, pipes or conduits 92, underwater locations 94, curves or bends 96, inside or outside of the aircraft system 122, the interior of pipe 126, and so on. The insertion tube 136 may include a head end section 138, an articulating section 140, and a conduit section 142. In the depicted embodiment, the head end section 138 may include a camera 144, one or more lights 146 (e.g., LEDs), and one or more measurement devices 148. In general, the head end section 138 may include one or more sensors that collect data about the surrounding environment (e.g., a camera 144, a measurement device 148, etc.) As mentioned above, the borescope's camera 144 may provide images and video suitable for inspection. The lights 146 may be used to provide for illumination when the head end section 138 is disposed in locations having low light or no light.

During use, the articulating section 140 may be controlled, for example, by the mobile device 30 and/or control inputs (e.g., relative control gestures) from the borescope 14. In particular, a set of relative control gestures may be used to control the articulating section 140. The articulating sections 140 may steer or "bend" in various dimensions, and may use pneumatic steering (i.e., one or more pneumatic cylinders), mechanical motors and wires, or a combination thereof to adjust the orientation of the head end section 138. For example, the articulation section 140 may enable movement of the head end section 138 in an X-Y plane X-Z plane and/or Y-Z plane of the depicted XYZ axes 150. Indeed, the relative control gestures may be used to perform control actions suitable for disposing the head end section 138 at a variety of angles, such as the depicted angle α. In this manner, the head end section 138 may be positioned to visually inspect desired locations. The camera 144 may then capture, for example, a video 152, which may be displayed in a screen 154 of the borescope 14 and a screen 156 of the mobile device 30, and may be recorded by the borescope 14 and/or the mobile device 30. In the depicted embodiments, the screens 154 and 156 may be multi-touch touch screens using capacitance techniques, resistive techniques, infrared grid techniques, and the like, to detect the touch of a stylus and/or one or more human fingers. Additionally or alternatively, images and the video 152 may be transmitted into the cloud 36.

Other data, including but not limited to sensor 148 data, may additionally be communicated and/or recorded by the borescope 14. The sensor 148 data may include temperature data, distance data, clearance data (e.g., distance between a rotating and a stationary component), flow data, and so on. In certain embodiments, the borescope 14 may include a plurality of replacement tips 158. For example, the replacement tips 158 may include retrieval tips such as snares, magnetic tips, gripper tips, and the like. The replacement tips 158 may additionally include cleaning and obstruction removal tools, such as wire brushes, wire cutters, and the like. The replacement tips 158 may additionally include tips having differing optical characteristics, such as focal length, stereoscopic views, 3-dimensional (3D) phase views, shadow views, and so on. Additionally or alternatively, the head end section 138 may include a removable and replaceable head end section 138. Accordingly, a plurality of head end sections 138 may be provided at a variety of diameters, and the insertion tube 136 maybe disposed in a number of locations having openings from approximately one millimeter to ten millimeters or more. Indeed, a wide variety of equipment and facilities may be inspected, and the data may be shared through the mobile device 30 and/or the cloud 36.

Figure 4:
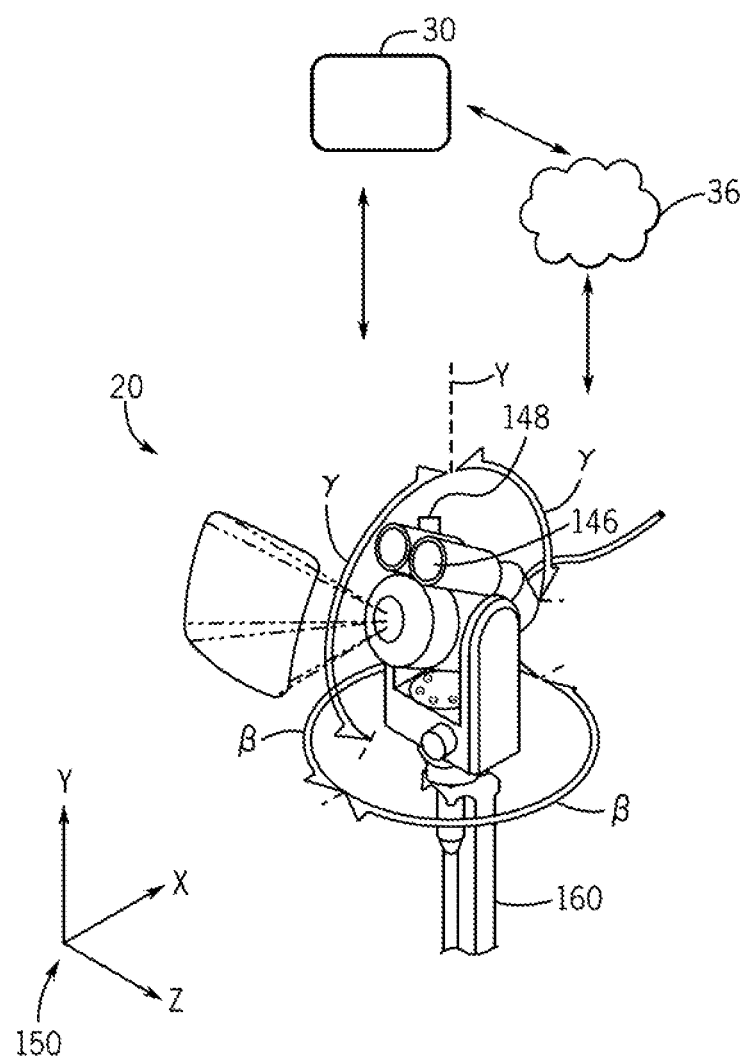
FIG. 4 is an illustration of an exemplary embodiment of a pan-tilt-zoom (PTZ) camera communicatively coupled to the mobile device of FIG. 1, in accordance with an embodiment of the present approach.

FIG. 4 is a perspective view of an embodiment of the transportable PTZ camera 20 communicatively coupled to the mobile device 30 and to the cloud 36. As mentioned above, the camera operator 42 may remotely manipulate the PTZ camera 20 to position the PTZ camera 20 to view desired equipment and locations. In the depicted example, the PTZ camera 20 may be tilted and rotated about the Y-axis. For example, the PTZ camera 20 may be rotated at an angle β between approximately 0° to 180°, 0° to 270°, 0° to 360°, or more about the Y-axis. Likewise, the PTZ camera 20 may be tilted, for example, about the Y-X plane at an angle γ of approximately 0° to 100°, 0° to 120°, 0° to 150°, or more with respect to the Y-Axis. Lights 146 may be similarly controlled, for example, to active or deactivate, and to increase or decrease a level of illumination (e.g., lux) to a desired value. Sensors 148, such as a laser rangefinder, may also be mounted onto the PTZ camera 20, suitable for measuring distance to certain objects. Other sensors 148 may be used, including long-range temperature sensors (e.g., infrared temperature sensors), pressure sensors, flow sensors, clearance sensors, and so on.

The PTZ camera 20 may be transported to a desired location, for example, by using a shaft 160. The shaft 160 enables the camera operator 42 to move the camera and to position the camera, for example, inside of locations 92, 126, underwater 94, into hazardous (e.g., hazmat) locations, and so on. Additionally, the shaft 160 may be used to more permanently secure the PTZ camera 20 by mounting the shaft 160 onto a permanent or semi-permanent mount. In this manner, the PTZ camera 20 may be transported and/or secured at a desired location. The PTZ camera 20 may then transmit, for example by using wired and/or wireless techniques, image data, video data, sensor 140 data, and the like, to the mobile device 30 and/or cloud 36. Accordingly, data received from the PTZ camera 16 may be remotely analyzed and used to determine the condition and suitability of operations for desired equipment and facilities.

Many NDT inspection devices 12 may include a physical joystick, physical control pad, and/or other physical gesticulation device, to control the movement of the articulating section or head end section of the device. Other NDT inspection devices 12 may use a virtual joystick, virtual control pad, and/or other virtual gesticulation device displayed on a screen associated with the device 12, such as the screen 154 of the borescope 14 or the screen 156 of the mobile device 30. However, there may be a limited number of control actions that can be assigned to the various movements of a control pad or joystick. For example, a physical joystick may only allow five movements (e.g., moving the joystick up, down, left, and right and pressing down on a button located on the joystick), and, accordingly only five control actions may be assigned to the physical joystick. There may also be a limited amount of customization that an operator (e.g., the borescope operator 38, the mobile device operator 40, the camera operator 42, etc.) may perform with regard to reassigning the control actions associated with the various movements.

To increase the number of control actions that may be assigned to a control system and the amount of customization for these mappings, the NDT inspection device 12 may use relative control gestures, as noted above. That is, certain control actions, such as moving the articulating section and/or head end section of an NDT inspection device 12, may be assigned to specific control gestures. In particular, the relative control gestures may map the movement of the head end section 138 of a borescope 14 in the depicted embodiments. Accordingly, the relative control gestures may be used in lieu of or in conjunction with a physical or virtual joystick or control pad.

The relative control gestures may be used to control many different modes of operation for the NDT inspection device 12 such as basic steering, steer and stay, and homing. The steer and stay mode of operation may trigger a freeze frame function for the head end section 138, and is described in further detail below. Homing typically refers to bringing the head end section 138 back to a "home" or neutral position. In certain embodiments, the relative control gestures may also be used to switch between the modes of operation for the NDT inspection device 12. As will be appreciated by the examples below, the relative control gestures are typically gestures whose interpretation is determined in part relative to a particular location on the touch-screen device. In one embodiment, the interpretation of the relative gestures is based on the proximity and direction of the gesture relative to the center of the screen. In other embodiments, corners of the screen, certain user-configurable screen areas(s), and so on, may be used alternative to or in addition to the center of the screen. For example, in some embodiments, the relative gestures may be interpreted relative to the center of an image representing the data collected by the head end section 138 and displayed on the screen 154. Accordingly, the relative control gestures may account for sensitivity control, as the interpretation of a relative control gesture is based on the proximity of the gesture relative to the center of the screen, the center of an image, and/or other screen areas.

Tables 1-3 below detail lists of exemplary relative control gestures and their assigned control actions for each of the three modes of operation. As will be appreciated, the lists in Tables 1-3 are not intended to be an exhaustive list of control actions, relative control gestures, and modes of operation for an NDT inspection device 12. Further, although the relative control gestures and control actions are described below with respect to a borescope 14, the relative control gestures and control actions may be used for any of the NDT inspection devices 12 (e.g., the PTZ camera 20, the eddy current inspection device 98, the ultrasonic flaw detector 100, and the digital radiography device 102). Additionally, while the relative control gestures are described below as being performed on a touch screen (e.g., screen 154 and/or screen 156), it should be appreciated that in other embodiments, the relative control gestures may be captured via a peripheral camera (e.g., a video camera) coupled to the borescope 14. In such embodiments, the relative control gestures may then be interpreted relative to a point in the viewing window of the camera; that is, relative to a point in the area captured by the camera.

Figure 5A:
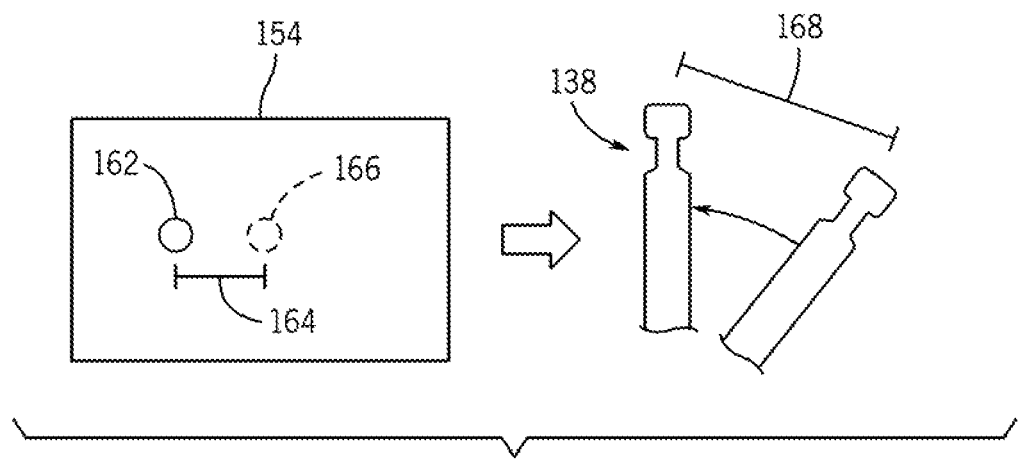
FIG. 5A is an illustration of an example of controlling the borescope of FIG. 3 using a relative control gesture, in accordance with an embodiment of the present approach.
Figure 5B:
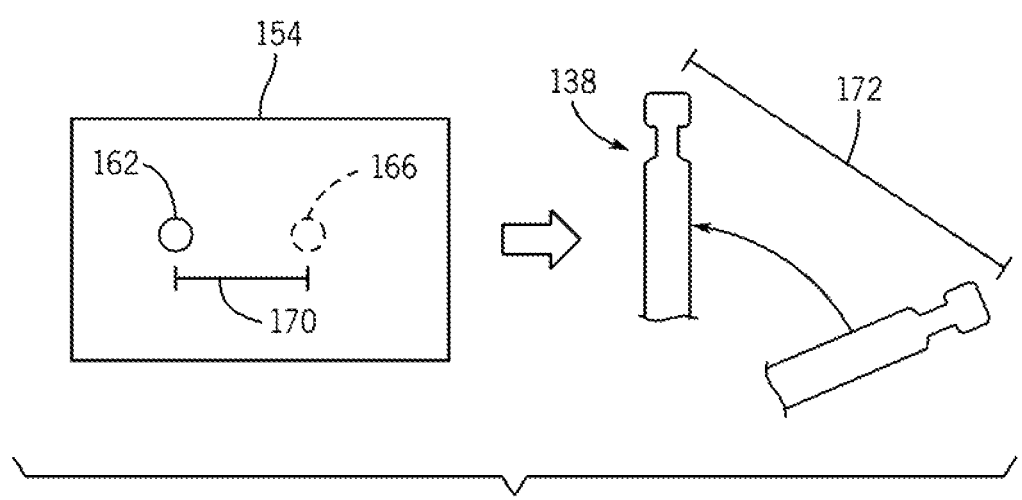
FIG. 5B is an illustration of another example of controlling the borescope of FIG. 3 using a relative control gesture, in accordance with an embodiment of the present approach.

Table 1 depicts exemplary relative control gestures and their respective control action for the basic steering mode of operation. A single tap gesture may be used to steer the head end section 138 and/or the articulating section 140 of the borescope 14 in a desired direction based upon the location of the tap relative to the center of the screen 154 of the borescope 14. The amount of distance between the starting position and the final position of the head section 138 may be determined based on the distance between the tap and the center of the screen 154. For example, as shown in FIG. 5A, a single tap 162 located at a distance 164 from the center 166 of the screen 154 may cause the head end section 138 to move a distance 168. In contrast, in FIG. 5B, the distance 170 is twice that of the distance 164 in FIG. 5A. Accordingly, the distance 172 in FIG. 5B can be twice that which is shown in FIG. 5A (although other scalings are possible).

TABLE 1

Relative Control Gestures and Control Actions for Basic Steering

| Relative Control Gesture | Control Action |
| --- | --- |
| Single Tap | Jog or bump in desired direction based on distance between tap and center of screen or current position |
| Double Tap | Jog or bump in desired direction based on distance between tap and center of screen or current position, larger distance or faster steering than single tap |
| Single Tap and Hold | Continuous steering in desired direction based on distance between tap and center of screen |
| Swipe Steering | Steering in desired direction, where the distance or steering speed is proportional to swipe speed or swipe length |
| Two Finger Drag (for devices having a camera) | Steering in desired direction and collecting images to create a panoramic image |

It is to be noted that while Tables 1-2 refer to the center of the screen as a start position, other start positions may include corners of the screen as well as a user customizable start position that may be anywhere on the screen. A double tap gesture may, like the single tap gesture, steer the head end section 138 and/or the articulating section 140 in a desired direction based on the location of the double tap relative to the center of the screen 154 and the distance between the double tap and the center of the screen 154. In some embodiments, the borescope 14 may be configured such that the head end section 138 covers a larger distance when a double tap is used than if a single tap was made in the same location. For instance, the head end section 138 may move a distance when a double tap is used that is twice the distance that would result from a single tap made in the same location. Accordingly, the double tap gesture may be used for significant changes in the orientation of the head end section 138 (e.g., for a 180° turn). In other embodiments, the double tap gesture may decrease the time used to steer the head end section 138 and/or the articulating section 140. That is, in such embodiments, the head end section 138 may cover the same distance based on the location of the gesture relative to the center of the screen 154 regardless of whether a single tap or double tap gesture is used. However, the borescope 14 may be configured such that using a double tap gesture steers the head end section 138 and/or the articulating section 140 to the desired location at faster rate (e.g., twice as fast) than the single tap gesture.

Figure 6A:
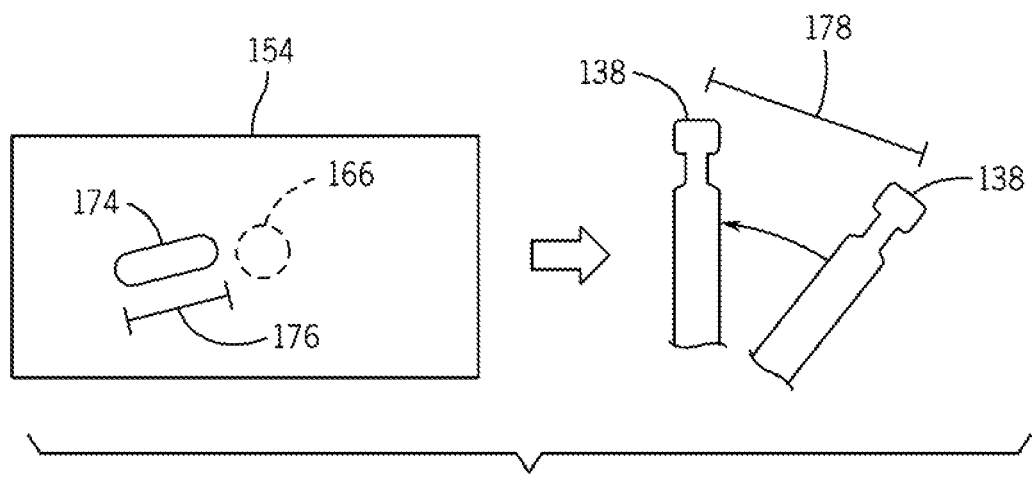
FIG. 6A is an illustration of another example of controlling the borescope of FIG. 3 using a relative control gesture, in accordance with an embodiment of the present approach.
Figure 6B:
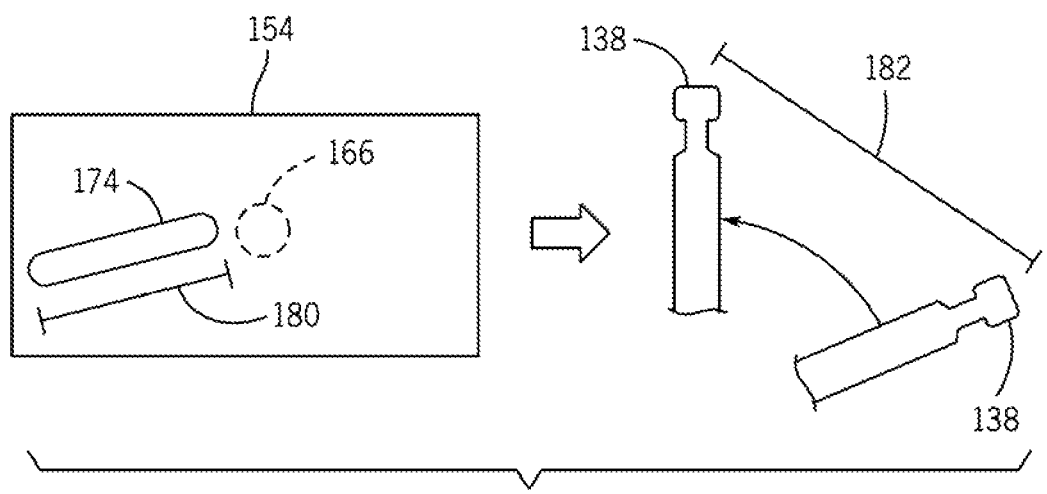
FIG. 6B is an illustration of another example of controlling the borescope of FIG. 3 using a relative control gesture, in accordance with an embodiment of the present approach.

A single tap and hold gesture may continuously steer the head end section 138 and/or the articulating section 140 in a desired direction based on the location of the tap relative to the center of the screen 154. A swipe steering gesture may steer the head end section 138 and/or the articulating section 140 in a desired direction based on the direction of a swipe. The distance covered by the head end section 138 may be proportional to either the length or speed of the swipe. For example, FIG. 6A depicts an embodiment in which a distance 178 covered by the head end section 138 is proportional to the length 176 of a swipe 174 on the screen 154 of the borescope 14. As shown, the length 180 in FIG. 6B is twice the length 176 in FIG. 6A, and as such, the distance 182 in FIG. 6B is twice the distance 178 in FIG. 6A. In other embodiments, a swipe steering gesture may affect both the distance covered by the head end section 138 as well as the speed of the steering. For example, the distance covered by the head end section 138 may be proportional to the length of the swipe, while the rate at which the head end section 138 and/or the articulating section 140 may be proportional to the speed of the swipe. Finally, in embodiments of NDT inspection devices 12 that include a camera, such as the borescope 14, a two finger drag gesture may steer the head end section 138 and/or the articulating section 140 in a desired direction while also collecting images during the movement to create a panoramic image or a partially panoramic image (e.g., image having a viewing angle between 90°-180°, 10°-270°, 0.5°-360°.

Table 2 depicts exemplary relative control gestures and the respective control actions when the borescope 14 is in the steer and stay mode of operation. Entering the steer and stay mode of operation may toggle a freeze frame function for the head end section 138. That is, once the head end section 138 is in a desired position, neither the head end section 138 nor the articulating section 140 may change position until the steer and stay mode of operation is exited, effectively locking the head end section 138 in place. As shown below, the two finger single tap; serial two finger tap; and single tap, hold, and tap gestures may operate similarly to the way they do in basic steering mode, and may toggle the freeze frame function once the control action is complete. Repeating any of the gestures may then cause the borescope 14 to exit the steer and stay mode of operation.

TABLE 2

Relative Control Gestures and Control Actions for Steer and Stay

| Relative Control Gesture | Control Action |
| --- | --- |
| Two Finger Single Tap | Steering in desired direction based on distance between tap and center of screen then lock in place; Exit mode |
| Serial Two Finger Tap | Steering in desired direction based on distance between tap and center of screen, then lock in place; Exit mode |
| Single Tap, Hold, Tap | Continuous steering in desired direction based on distance between tap and center of screen, then lock in place; Exit mode |

Finally, Table 3 lists exemplary relative control gestures and associated control actions for the homing mode of operation. As mentioned above, homing refers to steering the head end section 138 and/or the articulating section 140 such that the head end section 138 moves to a "home" or default position. Accordingly, most of the relative control gestures listed below (i.e., the two finger single tap and hold, tracing a counter-clockwise circle, a long hold, a single finger triple tap, and a swipe from the edge of the screen to the center of the screen) result in returning the head-end section 138 to the home position. Further, in some embodiments, a relative control gesture, such as tracing a clockwise circle, may result in returning the head end section 138 to its previous position before homing.

TABLE 3

Relative Control Gestures and Control Actions for Steer and Stay

| Relative Control Gesture | Control Action |
| --- | --- |
| Two Finger Single Tap and Hold | Return to home position |
| Trace a Counter-clockwise Circle | Return to home position |
| Long Hold | Return to home position |
| Single Finger Triple Tap | Return to home position |
| Swipe from Edge of Screen to Center of Screen | Return to home position |
| Trace a Clockwise Circle | Return to Last Position before homing |

As stated above, the relative control gestures and associated control actions listed in Tables 1-3 are not intended to be exhaustive nor are they intended to be restricted to borescopes 14. Indeed, the operator (e.g., the borescope operator 38, the mobile device operator 40, or the camera operator 42) may reassign the relative control gestures to other control actions or vice versa, and may also add additional relative control gestures and control actions. For example, the operator may assign control actions to relative control gestures that utilize a "hot corners" mechanism, in which the gesture occurs primarily within one corner of the screen. In other embodiments, the operator may assign control actions to relative control gestures that use multiple fingers, as shown above, or even multiple hands.

Figure 7:
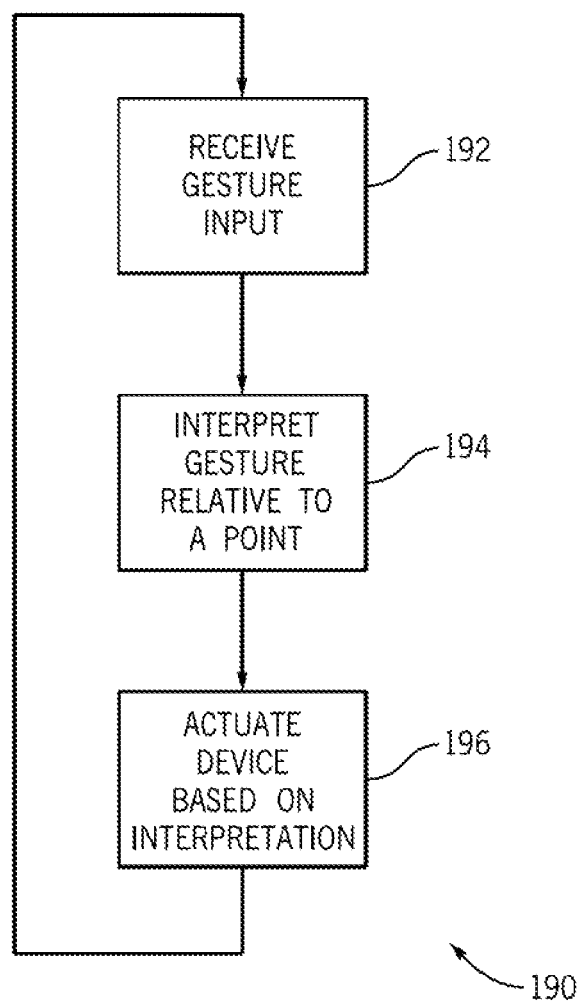
FIG. 7 is a flowchart illustrating an exemplary process for using relative control gestures to control the borescope of FIG. 3, in accordance with an embodiment of the present approach.

FIG. 7 depicts an exemplary process 190 for using relative control gestures to control the head end section 138 of the borescope 14 or any other suitable NDT device 12. Although the process 190 is described below in detail, the process 190 may include other steps not shown in FIG. 7. Additionally, the steps illustrated may be omitted, performed concurrently, and/or in a different order. The process 190 may be implemented as computer instructions or executable code stored in the memory 18 and executed by the processor 16 of the borescope 14, as described above.

Beginning at block 192, the borescope 14 may receive a relative control gesture as an input. As noted above, the relative control gestures may be received as touch-screen input via the screen 154 of the borescope 14 and/or the screen 156 of the mobile device 30. At block 194, the borescope 14 may then interpret the relative control gesture based on its proximity relative to a particular point on the screen 154 and/or 156, an image displayed on the screen 154 and/or 156, or other locations in the screen 154 and/or 156. For example, as noted above, the relative control gestures may include gestures that are interpreted relative to the center of the screen 154 as well as "hot corner" mechanisms that occur primarily within one corner of the screen 154. Finally, at block 196, the borescope 14 then steers the head end section 138 and/or the articulating section 140 to move the head end section 138 to the desired position based on the interpretation of the relative control gesture. Alternately or additionally, the borescope 14 may change its mode of operation based on the interpretation of the relative control gesture at block 196, as noted above.

Technical effects of the disclosure include controlling a non-destructive testing (NDT) device used to inspect equipment and facilities. In particular, the disclosed embodiments include using a set of relative control gestures to control a particular NDT device. The relative control gestures may be assigned to various control actions for controlling the orientation and/or movement of an NDT device. In certain embodiments, the relative control gestures may also be used to control the mode of operation of the NDT device. The relative control gestures and the control actions assigned to them may be customizable by an operator. The relative control gestures may also account for sensitivity control. Finally, the relative control gestures may be used to control an NDT device in lieu of or in conjunction with a physical control system. It should be noted that the embodiments described in the specification may have other technical effects and can solve other technical problems.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof "At least one of element A, element B, and element C" is not intended to be limited to at least one of an element A, at least one of an element B, and at least one of an element C.

This written description uses examples to disclose embodiments, including the best mode, and also to enable any person skilled in the art to practice the embodiments, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A non-destructive testing (NDT) system, comprising:
   a sensor configured to collect data about a surrounding environment;
   an articulating system configured to move the sensor;
   a touchscreen configured to display: i) a user interface and ii) an image of the surrounding environment based on the collected data, the touchscreen being configured to receive a plurality of control gestures; and
   a processor configured to:
      interpret at least one of the plurality of control gestures to derive a first touch area based on a user touching a first area of the touchscreen and to derive a first distance between the first area of the touchscreen and a point on the touchscreen; and
      control the articulating system to move the sensor a first movement distance based on the first distance.

2. The NDT system of claim 1, wherein the sensor includes at least one of a camera or a measurement device.

3. The NDT system of claim 1, wherein the touchscreen is located remotely from the sensor and the articulating system.

4. The NDT system of claim 3, wherein the system includes a display located proximate to the sensor and the articulating system.

5. The NDT system of claim 1, wherein the processor is configured to control a mode of operation of the sensor based on the interpretation of the plurality of control gestures.

6. The NDT system of claim 5, wherein the mode of operation includes at least one of steering or homing.

7. The NDT system of claim 1, wherein the touchscreen is configured to receive a user input to change a control action of the articulating system assigned to an interpretation of one of the plurality of control gestures.

8. The NDT system of claim 1, wherein the plurality of control gestures comprises selecting a corner of the image.

9. The NDT system of claim 1, wherein the sensor is configured as at least one of a borescope, a pan-to-zoom camera, an x-ray inspection device, an eddy current inspection device, and a digital radiography device.

10. The NDT system of claim 1, comprising a joystick device, a control-pad device, or any combination thereof, configured to control the orientation of the sensor.

11. A method, comprising:
collecting, via a non-destructive testing (NDT) system, data about a surrounding environment using a sensor;
constructing, via the NDT system, an image of the surrounding environment based on the collected data;
displaying the image on a touchscreen system;
receiving, via the touchscreen system, a control gesture as a user input;
interpreting the control gesture to derive a first touch area based on a user touching a first area of the touchscreen system and to derive a first distance between the first area of the touchscreen system and a point on the touchscreen system; and
controlling, via the NDT system, an articulating system coupled to the sensor to:
control an orientation of the sensor;
control a mode of operation of the sensor;
control a movement of the sensor;
or any combination thereof based on the interpretation of the control gesture.

12. The method of claim 11, wherein the point comprises a first point of the image, a center of the touchscreen system, or a corner arear of the touchscreen system.

13. The method of claim 11, comprising receiving a user input to change a control action of the articulating system or the control of a mode of operation assigned to the interpretation of the control gesture.

14. The method of claim 11, wherein the control gesture comprises a press and hold, and wherein controlling, via the NDT system, the articulating system comprises moving the sensor continuously towards the first area of the touchscreen system.

15. The method of claim 11, wherein the control gesture comprises a gesture using multiple fingers.

16. The method of claim 11, wherein the surrounding environment comprises an industrial equipment, an industrial facility, or a combination thereof.

17. A non-transitory, computer-readable medium comprising computer-executable code comprising instructions configured to:
receive data relating to an environment;
construct an image of the environment based on the received data;
display the image on a touch-screen device;
receive a control gesture via the touch-screen device;
interpret the control gesture to derive a first touch area based on a user touching a first area of the touch-screen device and to derive a first distance between the first area of the touch-screen device and a point on the touch-screen device;
control an articulating system coupled to the touch-screen device to control an orientation of a sensor configured to collect the data, control a mode of operation of the sensor, control a movement of the sensor, or any combination thereof based on the interpretation of the control gesture.

18. The non-transitory computer-readable medium of claim 17, wherein the sensor includes at least one of a camera or a measurement device.

19. The non-transitory computer-readable medium of claim 17, wherein the point comprises a first point of the image, a center of the touch screen device, or a corner arear of the touch-screen device.

20. The non-transitory computer-readable medium of claim 17, wherein the control gesture comprises a press and hold, and wherein the control the articulating system coupled to the touch-screen device comprises moving the sensor continuously towards the first area of the touch-screen device.

* * * * *